United States Patent [19]

Hao et al.

[11] Patent Number: 5,650,520
[45] Date of Patent: Jul. 22, 1997

[54] CRYSTAL MODIFICATION OF A DIKETOPYRROLOPYRROLE PIGMENT

[75] Inventors: Zhimin Hao, Marly; Ingo Schlöder, Matran; Abul Iqbal, Arconciel, all of Switzerland

[73] Assignee: Ciba-Geigy Corporation, Tarrytown, N.Y.

[21] Appl. No.: 493,516

[22] Filed: Jun. 22, 1995

[30] Foreign Application Priority Data

Jun. 29, 1994 [CH] Switzerland ................ 2075/94

[51] Int. Cl.$^6$ ................ C07D 487/04
[52] U.S. Cl. ................ 548/453
[58] Field of Search ................ 548/453

[56] References Cited

U.S. PATENT DOCUMENTS 4,415,685 11/1983 Iqbal et al. ................ 524/92
4,579,949 4/1986 Rochat et al. ................ 546/167

OTHER PUBLICATIONS

W. Herbst, K. Hunger: Industrial Organic Pigments pp. 41–43, pp. 427–428 & 453–454 (1993).
J. Mizuguchi et al., Acta Crystallograpica, vol. B48, Part 5, pp. 696–700, (1992).

Primary Examiner—Patricia L. Morris
Attorney, Agent, or Firm—Michele Kovaleski

[57] ABSTRACT

Diketopyrrolopyrrole of the formula

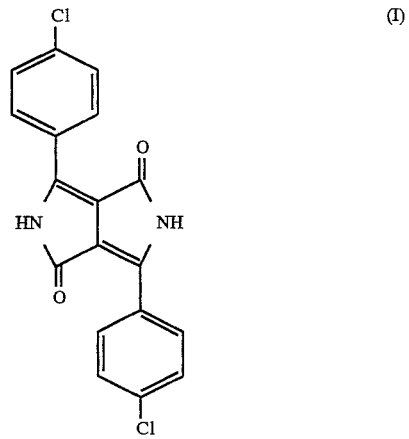

in its β-modification.

The new β-modification is likewise suitable as a pigment for coloring high-molecular weight organic material and, in comparison to the a-modification, shows a shift in shade towards yellowish-red.

10 Claims, No Drawings

CRYSTAL MODIFICATION OF A DIKETOPYRROLOPYRROLE PIGMENT

The present application relates to a new crystal modification of 1,4-diketo-3,6-bis(4-chlorophenyl)pyrrolo[3,4-c]pyrrole, to its preparation and the use of this new product as a pigment.

It is general knowledge that a number of representatives of different classes of organic pigments are polymorphous. Despite having the same chemical composition, such pigments occur in two or more crystal modifications. This is the case in particular for phthalocyanine, quinacridone and some azo pigments (cf. e.g. W. Herbst, K. Hunger, Industrial Organic Pigments (1993), 41–43, 427–428, 453–454). For some other pigments, in contrast, only one single crystal modification is known. For instance, despite a number of attempts it has hitherto been impossible to obtain, for any one of the diketopyrrolopyrrole pigments, which have been known for some years and are described, for example, in U.S. Pat. Nos. 4,415,685 and 4,579,949, a second crystal modification.

It has recently been found that leaving groups, for example those of the formula

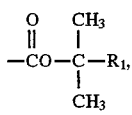

in which $R_1$ is $C_1$–$C_6$alkyl, can be introduced readily even into insoluble substances, like the diketopyrrolopyrrole pigments, with formation of soluble carbamates having the basic structure

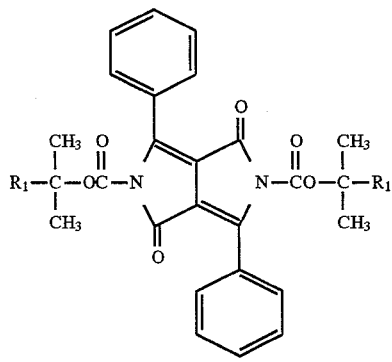

and that, by thermal (heating to temperatures of between 50° and 400° C.), chemical (with organic or inorganic acids or bases) or photolytic (exposure with, for example, wavelengths below 375 nm) treatment the original pigment can be reformed. These studies are described in parallel patent applications (application date October 1993).

Astonishingly it has now been found that, in the case of the diketopyrrolopyrrole of the formula

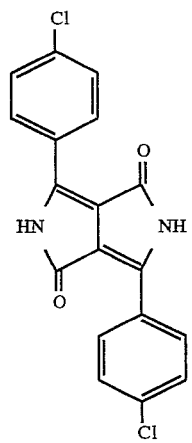

the abovementioned reformation of the (N-unsubstituted) pigment by chemical treatment under specific conditions leads not to the previously known modification but to a new crystal modification. The new modification, referred to hereinafter as the β-modification, differs from the known modification, referred to hereinafter as the α-modification, by a specific, different X-ray diffraction diagram, but also by a shift in shade towards yellowish-red, which shift is of interest for the utility as a pigment.

The complete X-ray diffraction patterns are determined by conventional methods using a Siemens D500® X-ray diffractometer (CuK$_\alpha$ radiation).

The X-ray diffraction pattern of the less yellowish known α-modification is characterized by the following diffraction lines

| Interplanar spacings (d values in Å) | double glancing angle (2Θ) | relative intensity |
|---|---|---|
| 11.7826 | 7.50 | 22 |
| 5.8252 | 15.20 | 19 |
| 3.6236 | 24.55 | 18 |
| 3.4612 | 25.72 | 41 |
| 3.3081 | 26.93 | 8 |
| 3.1570 | 28.25 | 100 |
| 2.8750 | 31.08 | 32 |
| 2.7828 | 32.08 | 17 |

The present invention relates to the diketopyrrolopyrrole of the formula

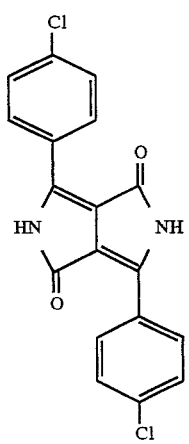

(I)

in its β-modification, whose X-ray diffraction pattern is characterized by the following diffraction lines

| Interplanar spacings (d values in Å) | double glancing angle (2Θ) | relative intensity |
|---|---|---|
| 15.2265 | 5.80 | 25 |
| 7.5110 | 11.77 | 27 |
| 6.5395 | 13.53 | 20 |
| 5.9710 | 14.82 | 42 |
| 5.0037 | 17.71 | 11 |
| 4.8711 | 18.20 | 12 |
| 3.8033 | 23.37 | 25 |
| 3.6411 | 24.43 | 14 |
| 3.2721 | 27.23 | 100 |
| 3.0229 | 29.53 | 27 |

This new β-modification is prepared by dissolving a soluble diketopyrrolopyrrole of the formula

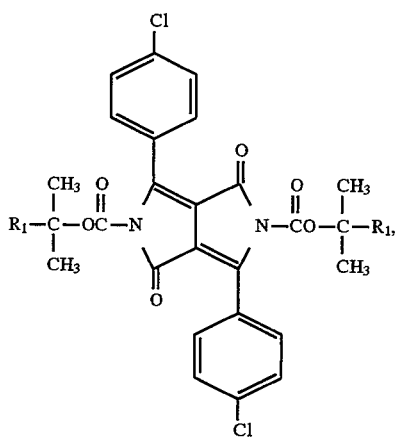

(II)

in which $R_1$ is $C_1$–$C_6$alkyl, in water and/or an organic solvent, heating the solution at a temperature of between 50° and 150° C. in the presence of an acid, and then isolating the product, which has precipitated after cooling, by conventional methods.

$R_1$ as $C_1$–$C_6$alkyl is for example methyl, ethyl, n-propyl, isopropyl, n-butyl, tert-butyl, n-amyl or hexyl.

$R_1$ is preferably ethyl, but especially methyl.

The dissolved diketopyrrolopyrrole of the formula II is advantageously treated in the presence of the acid under reflux for from 10 minutes to 20 hours, depending on the solvent, and the mixture is then advantageously cooled to from 10° to 30° C.

Solvents which can be used are water or inert aprotic organic solvents, for example dimethylformamide, tetrahydrofuran, ethylene glycol, ethylene glycol monomethyl ether, dodecane, toluene, xylene, acetylacetone, dimethyl sulfoxide or mixtures thereof. Preference is given to tetrahydrofuran or a dimethylformamide/water mixture, in particular in a ratio of about 2:1.

Suitable acids are both inorganic and organic acids, for example hydrochloric acid, sulfuric acid, toluenesulfonic acid or trifluoroacetic acid. 4-Toluenesulfonic acid is preferred. It is advantageous to employ from 10 to 30, preferably from 15 to 25 mol, of acid per mole of diketopyrrolopyrrole of the formula II. The acid can be added either before, together with or after the pigment salt suspension, preferably before or together with the pigment salt suspension.

It is preferred to use from 15 to 20 mol of 4-toluenesulfonic acid, based on the diketopyrrolopyrrole, under reflux in dimethylformamide/water 2:1 for from 15 to 45 minutes or in particular in tetrahydrofuran for from 8 to 16 hours.

Diketopyrrolopyrroles of the formula II can be obtained in analogy to generally known methods, for example by reacting a diketopyrrolopyrrole of the formula I with a dicarbonate of the formula

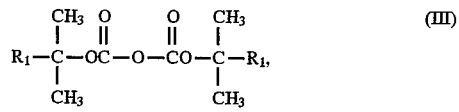

(III)

or with a trihaloacetic ester of the formula

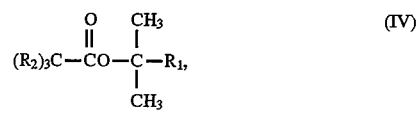

(IV)

in which $R_2$ is chlorine, fluorine or bromine, or with an azide of the formula

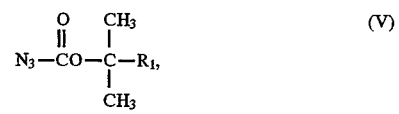

(V)

$R_1$ being in each case as defined above, in an aprotic organic solvent in the presence of a base as catalyst at temperatures of between 0° and 400° C. for from 2 to 80 hours.

The dicarbonate of the formula III, the trihaloacetic ester of the formula IV or the azide of the formula V is advantageously employed in a from 2- to 10-fold excess.

The diketopyrrolopyrrole of the formula I is preferably reacted with a dicarbonate of the formula III.

Dicarbonates of the formula III, trihaloacetic esters of the formula IV and azides of the formula V are known substances. Any that may be novel can be prepared in analogy to generally known methods.

Examples of suitable solvents are ethers, such as tetrahydrofuran or dioxane, or glycol ethers, such as ethylene glycol methyl ether, ethylene glycol ethyl ether, diethylene glycol monomethyl ether or diethylene glycol monoethyl ether, dipolar aprotic solvents, such as acetonitrile, benzonitrile, N,N-dimethylformamide, N,N-dimethylacetamide, nitrobenzene or N-methylpyrrolidone, halogenated aliphatic or aromatic hydrocarbons, such as trichloroethane, benzene or alkyl-, alkoxy- or halogen-substituted benzene, such as toluene, xylene, anisole or chlorbenzene, or aromatic nitrogen heterocycles, such as pyridine, picoline or quinoline. Examples of preferred solvents are tetrahydrofuran, N,N-dimethylformamide and N-methylpyrrolidone. The solvents mentioned may also be employed as mixtures. It is advantageous to use from 5 to 20 parts by weight of solvent per part by weight of the reactants.

Examples of bases which are suitable as catalysts are the alkali metals themselves, such as lithium, sodium or potassium and their hydroxides or carbonates, or alkali metal amides, such as lithium amide, sodium amide or potassium amide, or alkali metal hydrides, such as lithium hydride, sodium hydride or potassium hydride, or alkaline earth metal or alkali metal alcoholates which are derived, in particular, from primary, secondary or tertiary aliphatic alcohols of 1 to 10 carbon atoms, for example lithium, sodium or potassium methylate, ethylate, n-propylate, isopropylate, n-butylate, sec-butylate, tert-butylate, 2-methyl-2-butylate, 2-methyl-2-pentylate, 3-methyl-3- pentylate or 3-ethyl-3-pentylate, and also organic aliphatic, aromatic or heterocyclic nitrogen bases, including for example diazabicyclooctane, diazabicycloundecene and 4-dimethylaminopyridine, and trialkylamines, for example trimethylamine or triethylamine. It is also possible to use a mixture of the bases mentioned.

Preference is given to the organic nitrogen bases such as, for example, diazabicyclooctane, diazabicycloundecene and, in particular, 4-dimethylaminopyridine.

The reaction is preferably carried out at temperatures between 10° and 100° C., in particular between 14° and 40° C., and at atmospheric pressure.

In the meantime, however, it has been found that, in the preparation of the diketopyrrolopyrrole of the formula I by the conventional process, as described for example in U.S. Pat. No. 4,579,949, the β-modification is likewise obtained if very specific conditions are observed for the protonation of the pigment alkali metal salt and for the subsequent conditioning, i.e. if the pigment alkali metal salt suspension is discharged in a 1–2:1 volume mixture of an alcohol ROH in which R is $C_1$–$C_4$alkyl and water at a temperature between −20° and 20° C., preferably around 0° C., and is stirred in the presence of an acid in a quantity sufficient to maintain the pH at <7 at the same temperature, advantageously for example for from 10 minutes to 10 hours.

$C_1$–$C_4$Alkyl R is preferably methyl.

Examples of suitable acids are hydrochloric acid, sulfuric acid and acetic acid. Sulfuric acid is preferred.

Apart from small fluctuations in the positions of the reflections, which variations can be attributed to the limited resolution, the X-ray diffraction pattern of the product thus obtained corresponds to the X-my diffraction pattern of the β-modification.

The β-diketopyrrolopyrrole of the invention is also suitable, as already described, for example in U.S. Pat. Nos. 4,415,685 and 4,579,949 for its α-modification, as a pigment for colouring high molecular weight organic material. However, since it is transformed again into the α-modification on heating at temperatures which vary depending on the substrate, its use in materials which are processed at relatively high temperatures requires caution to be exercised.

Like many other pigments, the β-diketopyrrolopyrrole according to the invention can also be advantageously surface-treated by known methods in order to improve its properties in coating systems. Additives which are employed to reduce or avoid flocculation and to improve the dispersion stability can be used advantageously with the pigment according to the invention. The pigment treated in this way exhibits good properties, alone or mixed with other pigments, for the production of red masstone colorations in a variety of coating systems, but preferably in automotive finishing systems of the acrylic, alkyd and polyester type. 2-Phthalimidomethylquinacridone, quinacridonesulfonic acid and other similar derivatives are examples of deflocculating agents which can be used. In certain systems, the addition of polymeric dispersants may bring about an additional improvement in the properties of the pigment.

The β-diketopyrrolopyrrole according to the invention is employed in quantities of from 0.01 to 30% by weight, preferably from 0.1 to 10% by weight, based on the high molecular weight organic material to be coloured, and is incorporated into this material advantageously at temperatures between 20° and 180° C.

The β-diketopyrrolopyrrole according to the invention can be employed, for example, as a powder, paste, flush paste or formulation and is suitable, for example, for printing inks, sizing colours, binder colours or coatings of all kinds, such as physically and oxidatively drying coating materials, acid-, amine- and peroxide-curing coating materials or polyurethane coating materials. When the processing temperature permits it, the pigment can also be used for colouring synthetic, semisynthetic or natural macromolecular substances, alone or together with other organic or inorganic pigments. The resulting colorations, for example in coating materials, prints or plastics, are distinguished by a yellowish-red colour, good fastness to overspraying, migration, light and weathering, and by high tinctorial strength and transparency.

The pigment according to the invention can be used for colouring solid, elastic, pastelike, high-viscosity, low-viscosity or thixotropic materials and can be incorporated into these materials by methods which are known per se. For example, water-containing pastes can be obtained by stirring the pigment into water, with or without the addition of a wetting agent or dispersant, or by stirring or kneading the pigment into a dispersant in the presence of water and in the presence or absence of organic solvents or oils. These pastes can be employed in turn, for example, to produce flush pastes, printing inks, sizing colours and polymer dispersions. However, the pigment can also be introduced by stirring, rolling, kneading or grinding into water, organic solvents, non-drying oils, drying oils, coating materials, plastics or rubber. Finally, it is also possible to process the pigment by dry mixing with organic or inorganic materials, .granules, fibrous substances, powders and other pigments, to give compositions.

The examples which follow illustrate the invention.

EXAMPLE 1a (Preparation of the soluble diketopyrrolopyrrole)

1.78 g of 4-dimethylaminopyridine and then 26.8 g of di-tert-butyl dicarbonate are added to a suspension of 20.0 g of 1,4-diketo-3,6-di(4-chlorophenyl)-pyrrolo[3,4-c]pyrrole in 500 ml of N,N-dimethylformamide (dried over molecular sieve). The reaction mixture is stirred at room temperature with exclusion of atmospheric moisture. After 15 hours, a further 26.8 g of di-tert-butyl dicarbonate are added and stirring is continued for 30 hours. The brown-orange product which has precipitated is filtered off, washed with methanol and dried in vacuo at room temperature, to give 21.8 g (70% of theory) of the product of the formula

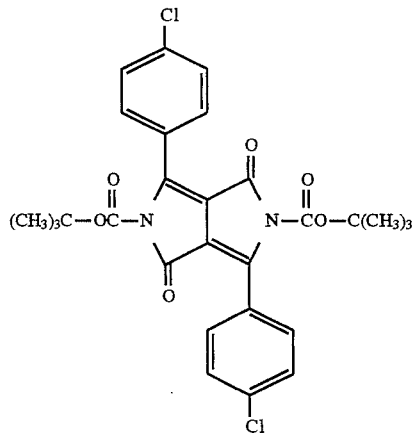

| Analysis: | C | H | N | Cl |
|---|---|---|---|---|
| Calc.: | 60.33% | 4.70% | 5.03% | 12.72% |
| Found: | 60.24% | 4.79% | 4.92% | 12.50% | b) A mixture of 1.5 g of the product from a) and 5.1 g of 4-toluenesulfonic acid monohydrate in 75 ml of tetrahydrofuran is stirred under reflux for 15 hours and then cooled to 30° C. The precipitated pigment is filtered off, washed with methanol and then with water, and dried to give 0.55 g (57.2% of theory) of a red powder.

| Analysis: | C | H | N | Cl |
|---|---|---|---|---|
| Calc.: | 60.53% | 2.82% | 7.84% | 19.85% |
| Found: | 60.38% | 2.96% | 7.69% | 19.42% |

The X-ray diffraction pattern is characterized by the following diffraction lines

| Interplanar spacings (d values in Å) | double glancing angle (2Θ) | relative intensity |
|---|---|---|
| 15.2265 | 5.80 | 25 |
| 7.5110 | 11.77 | 27 |
| 6.5395 | 13.53 | 20 |
| 5.9710 | 14.82 | 42 |
| 5.0037 | 17.71 | 11 |
| 4.8711 | 18.20 | 12 |
| 3.8033 | 23.37 | 25 |
| 3.6411 | 24.43 | 14 |
| 3.2721 | 27.23 | 100 |
| 3.0229 | 29.53 | 27 |

EXAMPLE 2

170 ml of tert-amyl alcohol are placed under nitrogen in a sulfonating flask. Following the addition of 14.72 g of sodium, the mixture is heated to 92°–102° C. The molten sodium is maintained overnight at 100°–107° C. with vigorous stirring. Then 44.02 g of 4-chlorobenzonitrile and 37.2 g of diisopropyl succinate dissolved in 50 ml of tert-amyl alcohol at 80° C. are metered into the solution formed, over the course of 2 hours at 105° C. Stirring of the reaction mixture is continued for 3 hours at 101°–105° C., and at the same time 4.88 g of diisopropyl succinate are added. The reaction mixture is subsequently cooled to room temperature, discharged into a mixture of 270 ml of methanol, 200 ml of water and 64.1 g of concentrated sulfuric acid at 0° C. and then stirred at 0° C. for 6 hours. The red mixture is filtered off, washed with methanol and then with water and dried at 80° C. in a vacuum drying oven, to give 52.3 g of a red powder.

| Analysis: | C | H | N | Cl |
|---|---|---|---|---|
| Calc.: | 60.53% | 2.82% | 7.84% | 19.85% |
| Found: | 60.29% | 2.79% | 7.60% | 19.24% |

The X-ray diffraction pattern is characterized by the following diffraction lines

| Interplanar spacings (d values in Å) | double glancing angle (2Θ) | relative intensity |
|---|---|---|
| 15.2765 | 5.78 | 25 |
| 7.5209 | 11.76 | 27 |
| 6.5400 | 13.53 | 20 |
| 5.9813 | 14.80 | 43 |
| 5.0006 | 17.72 | 12 |
| 4.8742 | 18.19 | 12 |
| 3.8011 | 23.38 | 25 |
| 3.6402 | 24.43 | 15 |
| 3.2716 | 27.23 | 100 |
| 3.0217 | 29.53 | 27 |

EXAMPLE 3

1.0 g of the pigment prepared according to Example 1b are mixed with 63.0 g of polyvinyl chloride, 3.0 g of epoxidized soya oil, 2.0 g of barium/cadmium thermal stabilizer and 32.0 g of dioctyl phthalate, and the mixture is processed on a roller mill at 160° C. for 8 minutes to give a thin sheet. The red PVC sheet produced in this way is distinguished by very good colour properties and outstanding fastness to heat, light and migration.

EXAMPLE 4

A mixture of 460 g of steatite balls of 8 mm in diameter, an alkyd varnish consisting of 58.7 g of alkyd resin ®ALKYLDAL F 310 (Bayer AG), 60% in xylene, 58.7 g of alkyd rosin ®ALKYLDAL F 32 (Bayer AG), 60% in xylene, 2.0 g of ®Silikonöl [silicone oil]A (Bayer AG), 1% in xylene, 4.0 g of n-butanol, 4.0 g of. ®DOWANOL (Dow Chem), 15 g of xylene, 5.6 g of dispersant ®DISPERBYK D-160 (BYK-Chemie) and also 28.0 g of the pigment prepared according to Example 1b are dispersed in a glass bottle with a twist-off cap on a roller frame for 72 hours. Following addition of 24.0 g of the melamine component ®CYMEL 327 (cyanamide) 90% in xylene, dispersion on the roller frame is continued for one hour. The steatite balls are then separated off. The resulting paint dispersion is applied to ®MILAR transparent sheets and then baked for 30 minutes at 130° C. (coat thickness 50 μm). A red colouration is obtained which has excellent colour properties.

What is claimed is:

1. A diketopyrrolopyrrole of the formula

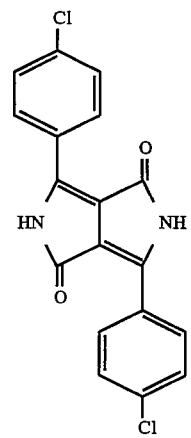

(I)

in its β-modification, whose X-ray diffraction pattern is characterized by the following diffraction lines

| Interplanar spacings (d values in Å) | double glancing angle (2ϑ) | relative intensity |
|---|---|---|
| 15.2265 | 5.80 | 25 |
| 7.5110 | 11.77 | 27 |
| 6.5395 | 13.53 | 20 |
| 5.9710 | 14.82 | 42 |
| 5.0037 | 17.71 | 11 |
| 4.8711 | 18.20 | 12 |
| 3.8033 | 23.37 | 25 |
| 3.6411 | 24.43 | 14 |
| 3.2721 | 27.23 | 100 |
| 3.0229 | 29.53 | 27 |

2. A process for the preparation of a diketopyrrolopyrrole according to claim 1, which comprises dissolving a soluble diketopyrrolopyrrole of the formula

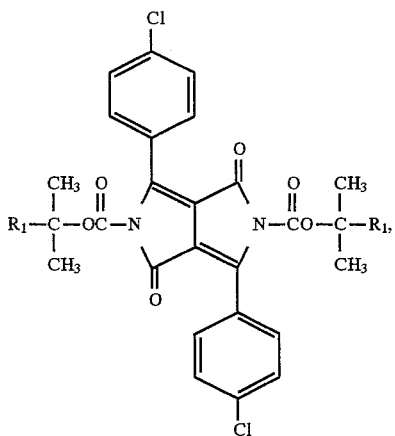
(II)

in which $R_1$ is $C_1$–$C_6$alkyl, in water or an organic solvent with or without water, heating the solution at a temperature of between 50° and 150° C. in the presence of an acid, and then isolating the product, which has precipitated after cooling.

3. A process according to claim 2, wherein a compound of the formula II is used in which $R_1$ is ethyl or methyl.

4. A process according to claim 2, wherein the diketopyrrolopyrrole of the formula 11 is treated under reflux for from 10 minutes to 20 hours and the mixture is then cooled to from 10° to 30° C.

5. A process according to claim 4, wherein the solvent used is tetrahydrofuran or a dimethylformamide/water mixture.

6. A process according to claim 2, wherein the acid used is 4-toluenesulfonic acid.

7. A process according to claim 2, wherein from 10 m 30 mol of acid are employed per mole of diketopyrrolopyrrole of the formula II.

8. A process according to claim 2, wherein the diketopyrrolopyrrole of the formula II is treated with from 15 to 20 mol of 4-toluenesulfonic acid, based on the diketopyrrolopyrrole, under reflux in dimethylformamide/water 2:1 for from 15 to 45 minutes.

9. A process according to claim 2, wherein the diketopyrrolopyrrole of the formula II is treated with from 15 to 20 mol of 4-toluenesulfonic acid, based on the diketopyrrolopyrrole, in tetrahydrofuran for from 8 to 16 hours.

10. A process according to claim 3, wherein a compound of formula II is used in which $R_1$ is methyl.

* * * * *